US006127173A

United States Patent [19]
Eckstein et al.

[11] Patent Number: 6,127,173
[45] Date of Patent: Oct. 3, 2000

[54] NUCLEIC ACID CATALYSTS WITH ENDONUCLEASE ACTIVITY

[75] Inventors: Fritz Eckstein, Göttingen, Germany; Paul A. Heaton, Warrington, United Kingdom; Narendra K. Vaish, Brighton, Mass.

[73] Assignee: Ribozyme Pharmaceuticals, Inc., Boulder, Colo.

[21] Appl. No.: 09/159,274

[22] Filed: Sep. 22, 1998

Related U.S. Application Data

[60] Provisional application No. 60/059,473, Sep. 22, 1997.
[51] Int. Cl.[7] ............................. C12Q 1/68; C12P 19/34; C12N 15/00; C12N 5/00
[52] U.S. Cl. ........................ 435/320.1; 435/6; 435/91.1; 435/91.31; 435/325; 435/375; 536/23.1; 536/23.2
[58] Field of Search ................................. 536/23.1, 23.2, 536/24.5; 435/320.1, 91.1, 91.31

[56] References Cited

U.S. PATENT DOCUMENTS

| | | | |
|---|---|---|---|
| 5,298,612 | 3/1994 | Jennings et al. | 536/23.2 |
| 5,334,711 | 8/1994 | Sproat et al. | 536/24.5 |
| 5,624,803 | 4/1997 | Noonberg et al. | 435/6 |
| 5,688,670 | 11/1997 | Szostak et al. | 435/91.21 |
| 5,807,718 | 9/1998 | Joyce et al. | 435/91.5 |
| 5,861,501 | 1/1999 | Benseler et al. | 536/24.5 |

FOREIGN PATENT DOCUMENTS

| | | |
|---|---|---|
| 89/02439 | 3/1989 | WIPO . |
| 91/03162 | 3/1991 | WIPO . |
| 92/07065 | 4/1992 | WIPO . |
| 93/15187 | 8/1993 | WIPO . |
| 93/23569 | 11/1993 | WIPO . |
| 94/02595 | 2/1994 | WIPO . |
| 95/06731 | 3/1995 | WIPO . |
| 95/11910 | 5/1995 | WIPO . |
| 96/10390 | 4/1996 | WIPO . |
| 96/10391 | 4/1996 | WIPO . |
| 96/10392 | 4/1996 | WIPO . |
| 96/18736 | 6/1996 | WIPO . |

OTHER PUBLICATIONS

Bartel and Szostak, "Isolation of New Ribozymes From a Large Pool of Random Sequences," *Science* 261:1411–1418 (1993).

Beaudry and Joyce, "Directed Evolution of an RNA Enzyme, " *Science* 257:635–641 (1992).

Beaudry and McSwiggen, "Quantitation of Ribozyme Target Abundance by QCPCR," *Methods of Molecular Biology* 74(34):325–339.

Been et al., "Secondary Structure of the Self–Cleaving RNA of Hepatitis Delta Virsus: Applications to Catalytic RNA Design, " *Biochemistry* 31:11843–11852 (1992).

Beigalman et al., "Chemical Modification of Hammerhead Ribozymes, " *J. Biol. Chem.* 270:25702–25708 (1995).

Beigalman et al., "Synthesis of 1–Deoxy–D–Ribofuranose Phosphoramidite & The Incorporation of Abasic Nucleotides in the Stem–Loop II of a Hammerhead Ribozyme," *Bioorganic & Medicinal Chemistry Letters* 4:1715–1720 (1994).

Benseler et al., "Hammerhead–like Molecules Containing Non–Nucleoside Linkers Are Active RNA Catalysts," *J. Am. Chem. Soc.* 115:8483–8484 (1993).

Breaker and Joyce, "Inventing and improving ribozyme function: rational design versus iterative selection methods," *TIBTECH* 12:268–275 (1994).

Andrea D. Branch, A good antisense molecule is hard to find, TIBS, 47–48, Feb. 1998.

Trisha Gura, antisense Has Growing Pains, Science, pp. 575–577, Oct. 1995.

Stanley Crooke, Antisense '97: A roundtable on the state of the industry, Nature Biotechnology, p. 522, Jun. 1997.

Stanley Crooke, Antisense Research and Applications, Chapter 1, Basic Principles of Antisense Therapeutics, Springer–Verlag Press, Berlin, Heidelberg, New York, P. 3, Jul. 1998.

Breaker, "Are engineered proteins getting competition from RNA?" *Current Opinion in Biotechnology* 7:442–448 (1996).

Burgin et al., "Chemically modified hammerhead ribozymes with improved catalytic rates," *Biochemistry* 35:14090–14097 (1996).

Cech, "Ribozyme Engineering, " *Current Opinion in Structural Biology* 2:605–609 (1992).

Cech, "Ribozymes and Their Medical Implications," *JAMA* 260:3030–3034 (1988).

Chen et al., "Multitarget–Ribozyme Directed to Cleave at up to Nine Highly Conserved HIV–1 env RNA Regions Inhibits HIV–1 Isolates, " *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes, " *J.Biol. Chem.* 269:25856–25864 (1994).

Christoffersen and Marr, "Ribozymes as Human Therapeutic Agents, " *J. Med. Chem.* 38:2023–2037 (1995).

Cload and Schepartz, "Polyether Tethered Oligonucleotide Probes, " *J. Am. Chem. Soc.* 113:6324–6326 (1991).

Couture and Stinchcomb, "Anti–gene therapy: the use of ribozymes to inhibit gene function," *Trends In Genetics* 12:510–515 (1996).

Dropulic et al., "Functional Characterization of a U5 Ribozyme: Intracellular Suppression of Human Immunodefiency Virus Type I Expression ," *Journal of Virology* 66:1432–1441 (1992).

(List continued on next page.)

*Primary Examiner*—Robert A. Schwartzman
*Assistant Examiner*—Janet Epps

[57] ABSTRACT

Nucleic acid molecules with new motifs having catalytic activity, methods of synthesis, and use thereof are also described.

28 Claims, 9 Drawing Sheets

OTHER PUBLICATIONS

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353–6359 (1990).

Elroy–Stein and Moss, "Cytoplasmic Expression System Based on Constitutive Synthesis of Bacteriophage T7 RNA Polymerase in Mammalian Cells,"*Proc. Natl. Acad. Sci. USA* 87:6743–6747 (1990).

Ferentz and Verdine, "Disulfied Cross–Linked Oligonucleotides," *J. Am. Chem. Soc.* 113:4000–4002 (1991).

Forster and Symons, "Self–Cleavage of Plus and Minus RNAs of a Virusoid and a Structural for the Active Sites," *Cell* 49:211–220 (1987).

Frank et al., "In vitro selection of Rnase P RNA reveals optimized catalytic activity in a highly conserved structural domain, " *RNA* 2:1179–1188(1996).

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Gold et al., Diversity of Oligonucleotide Functions, *Annu. Rev. Biochem.* 64:763–797 (1995).

Good et al., "Expression of small, therapuetic RNAs in human nuclei," *Gene Therapy* 4:45–54 (1997).

Guo and Collins, "Efficent Trans–cleavage of a stem–loop RNA substrate by a ribozyme derived from Neurospora VS RNA," *EMBO J.* 14:368–376 (1995).

Hendry et al., "Using linkers to investigate the spatial separation of the conserved nucleotides $A_9$ and $G_{12}$ in the Hammerhead Ribozyme," *Biochemica et Biophysica Acta* 1219:405–412 (1994).

Hertel et al., "A Kinetic Thermodynamic Framework for the Hammerhead Ribozyme Reaction," *Biochemistry* 33:3374–3385 (1994).

Hodgson et al., "Probing the hammerhead robozyme structure with ribonucleases," *Nucleic Acids Research* 22:1620–1625 (1994).

Igloi et al., "Interaction of tRNAs and of Phosphorothioate--Substituted Nucleic Acids with an Organomercurial. Probing the Chemical Environment of Thiolated Residues by Affinity Electrophoresis," *Biochemistry* 27:3842–3849 (1988).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995).

Ishizaka et al., "Isolation of Active Ribozymes from an RNA Pool of Random Sequences Using an Anchored Substrate RNA," *Biochemical and Biophysical Research Communication* 214(2):403–409 (1995).

Izant and Weintraub, "Constitutive and Conditional Suppression of Exogenous and Endogeneous Genes by Anti--Sense RNA, " *Science* 229:345–352 (1985).

Jäschke et al., "Automated Incorporation of Polyethylene Glycol into Synthetic Oligonucleotides," *Tetrahedron Letters* 34:301–304 (1993) (Jaschke).

Jeffries and Symons, "A Catalytic 13–mer Ribozyme," *Nucleic Acids Research* 17:1371–1377 (1989) (also referred to as Jefferies).

Joseph and Burke, "Optimization of an Anti–HIV Hairpin Ribozyme by in Vitro Selection," *J. Biol. Chem.* 268:24510–24518 (1993).

Joyce et al., "Amplication, Mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–ras Ribozyme," *Anitsense Research & Development* 2:3–15 (1992).

Kumar and Ellington,"Artificial evolution and natural ribozymes," *FASEB J.* 9:1183–1195 (1995).

Lasic and Needham "The 'Steath' Liposome: A Prototypical Biomaterial," *Chemical Reviews* 95:2601–2627 (1995).

Lasic and Papahadjopoulos, "Liposomes Revisited," *Science* 267:1275–1276 (1995).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA, " *Nucleic Acids Research* 22(12):2183–2196 (1994).

Lisziewicz et al., "Inhibition of Human Immunodeficiency Virus Type 1 Replication by Regulated Expression of a Polymeric Tat Activation Response RNA Decoy as a Stategy for Gene Therapy in AIDS," *Proc. Natl. Acad. Sci. U.S.A.* 90:8000–8004 (1993).

Liu et al., "Cationic Liposome–mediated Intravenous Gene Delivery," *J. Biol. Chem.* 270(42):24864–24870 (1995).

Long and Uhlenbeck, "Kinetic characterization of intramolecular and intermolecular hammerhead RNAs with stem II deletions," *Proc. Natl. Acad. Sci. USA* 91:6977–6981 (1994).

Loria and Pan, "Domain Structure of the ribozyme from eubacterial ribonuclease P," *RNA* 2:551–563 (1996).

Ma et al., "Design and Sythesis of RNA Miniduplexes via a Synthetic Linker Approach. 2. Generation of Convalently Closed, Double–Stranded Cyclic HIV–1 TAR RNA Analogs with High Tat–Binding Affinity, " *Nucleic Acids Research* 21:2585–2589 (1993).

Ma et al., "Design and Synthesis of RNA Miniduplexes via a Synthetic Linker Approach," *Biochemistry* 32:1751–1758 (1993).

McCall et al., "Minimal sequence requirements for ribozyme activity, " *Proc. Natl. Acad. Sci. USA* 89:5710–5714 (1992).

McCurdy et al., "Deoxyoligonucleotides with Inverted Polarity: Synthesis and Use in Triple–Helix Formation" *Nucleosides & Nucleotides* 10:287–290 (1991).

McGarry and Lindquist, "Inhibition of heat shock protein synthesis by heat–inducible antisense RNA," *Proc. Natl. Acad. Sci. USA* 83:399–403 (1986).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan and Uhlenbeck, "Synthesis of Small RNAs Using T7 RNA Polymerase," *Methods Enzymol.* 180:51–62 (1989).

Nakamaye and Eckstein, "AUA–Cleaving Hammerhead Ribozymes: Attempted Selection for Improved Cleavage," *Biochemistry* 33:1271–1277 (1994).

Nathans and Smith, "Restrictions Endonucleases in the Analysis and Restructuring of DNA Molecules," *Ann. Rev. Biochem.* 44:273–293 (1975).

Noonberg et al., In vivo generation of highly abundant sequence–specific oligonucleotides for antisense and triplex gene regulation, *Nucleic Acids Research* 22(14):2830–2836 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Oku et al., "Real–time analysis of liposomal trafficking in tumor–bearing mice by use of positron emission tomography," *Biochimica et Biophysica Acta* 1238:86–90 (1995).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

Orgel, "Selection in vitro," *Proc. R. Soc. London B.* 205:435–442 (1979).

Pan et al., "Properties of an In Vitro Selected $Pb^{2+}$ Cleavage Motif," *Biochemistry* 33:9561–9565 (1994).

Perreault et al., "Mixed Deoxyribo–and Ribo–Oligonucleotides with Catalytic Activity," *Nature* 344:565–567 (1990) (often mistakenly listed as Perrault).

Pieken et al., "Kinetic Characterization of Ribonuclease–Resistant 2'–Modified Hammerhead Ribozymes," *Science* 253:314–317 (1991).

Pley et al.,."Three–dimensional structure of a hammerhead ribozyme," *Nature* 372:68–74 (1994).

Richardson and Schepartz, "Tethered Oligonucleotide Probes. A Strategy for the Recognition of Structured RNA," *J. Am. Chem. Soc.* 113:5109–5111 (1991).

Ruffner et al., "Sequence Requirements of the Hammerhead RNA Self–Cleavage Reaction," *Biochemistry* 29:10695–10702 (1990).

Sarver et al., "Ribozymes as Potential Anti–HIV–1 Therapeutic Agents" *Science* 247:1222–1225 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using — cyanoethyl protected ribonucleoside phosphoramidites," *Nucl Acids Res.* 18:5433–5441 (1990).

Scott et al., "Capturing the Structure of a Catalytic RNA Intermediate: The Hammerhead Ribozyme, " *Science* 274:2065–2069 (1996).

Seela and Kaiser, "Oligodeoxyribonucleotides containing 1,3–propanediol as nucleoside substitute," *Nucleic Acids Research* 15:3113–3129 (1987).

Sugiyama et al., "Catalytic activities of hammerhead ribozymes with a triterpenoid linker instead of stem/loop II," *FEBS Letters* 392:215–219 (1996).

Sullenger and Cech,"Tethering Ribozymes to a Retroviral Packaging Signal for Destruction of Viral RNA," *Science* 262:1566–1569 (1993).

Szostak and Ellington, "Ch. 20 –In Vitro Selection of Functional RNA Sequences,"in *The RNA World,* edited by Gesteland and Atkins, Cold Spring Harbor Laboratory Press, pp. 511–533 (1993).

Szostak, "In Vitro Genes," *TIBS* 17:89–93 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tang et al., "Examination of the catalytic fitness of the hammerhead ribozyme by in vitor selection," *RNA* 3:914–925 (1997).

Thompson et al., "Improved accumulation and activity of ribozymes expressed from a tRNA–based RNA polymerase III promoter," *Nucleic Acids Research* 23:2259–2268 (1995).

Thomson et al., "In vitro selection of hammerhead ribozymes containing a bulged nucleotide in stem II," *Nucleic Acids Research* 24:4401–4406 (1996).

Usman and Cedergren, "Exploiting the chemical synthesis of RNA," *TIBS* 17:334–339 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Vaish et al., "Isolation of Hammerhead Ribozymes with Altered Core Sequences by in Vitro Selection," *Biochemistry* 36:6495–6501 (1997).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–5534 (1994).

Wincott et al., "Synthesis, deprotection, analysis and purification of RNA and ribozymes," *Nucleic Acids Research* 23:2677–2684 (1995).

Yarus, "A Specific Amino Acid Binding Site Composed of RNA," *Science* 240:1751–1758 (1988)

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

5´-GGGAGACUGUCUAGAUCAUGAGGAGUCUAAUCCU NNNNNNN NNNNNNNNNN NNN AUGAUCUGCAGGAUCC-3´

| CLONE NO. | | | | | $k_{in\text{-}cis}$ (min-1) |
|---|---|---|---|---|---|
| wt HAMMERHEAD RIBOZYME | | CUGAUG | AGCCGCAAGC | GAA | 0.66 |
| POOL 7 | 14 | GGAAUC | AGCCUGACACCGG | CCC | 0.03 |
| POOL 10 | 18 | GGCAUC | CCCGGCAUGGUGC | GCG | 0.06 |
| POOL 13 | 31 | AGCAUU | ACCCGGCUGGUGC | GCG | 0.20 |
| | 29 (2x) | GCAUCA | CGGGGCAAUCUGC | GCG | 0.16 |
| | 18 (2x) | AGCAUC | ACCCGGCUGGUGC | GCG | 0.08 |
| | 36 | AGCAUC | ACCCGGCUGGUGC | GCG | 0.08 |
| | 39 | AGCGUC | CACGGCAUCGAGC | GCG | 0.04 |
| | 19 | UGAUG | GCUUGCACUAAGC | GCG | 0.83 |
| | 40 (2x) | UGAUG | GCAUGCACUAUGC | GCG | 0.52 |
| | 4 | UGAUG | GCAUGCAGGAUGC | GCG | 0.47 |
| | 21 | UGAUG | GCAUGCACCAUGC | GCG | 0.33 |
| | 1 | UGAUC | GGAUGCACCAUCG | GCG | 0.24 |
| | 3 | UGGGC | CGAUCGCAAGGGC | GCG | 0.03 |

FIG. 3

SEQUENCE LISTING

```
<160> NUMBER OF SEQ ID NOS: 38

<210> SEQ ID NO 1
<211> LENGTH: 57
<212> TYPE: DNA
<213> ORGANISM: Artificial Sequence
<220> FEATURE:
<223> OTHER INFORMATION: Synthesized nucleic acid molecule

<400> SEQUENCE: 1
tggtgcaagc ttaatacgac tcactatagg gagactgtct agatcatgag gatgcta        57

<210> SEQ ID NO 2
<211> LENGTH: 59
<212> TYPE: DNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or t.

<400> SEQUENCE: 2
tctcggatcc tgcagatcat nnnnnnnnnn nnnnnnnnnn nnaggattag catcctcat        59

<210> SEQ ID NO 3
<211> LENGTH: 20
<212> TYPE: DNA
<213> ORGANISM: Artificial Sequence
<220> FEATURE:
<223> OTHER INFORMATION: Synthesized nucleic acid molecule
```

<400> SEQUENCE: 3
tctcggatcc tgcagatcat                                                   20

<210> SEQ ID NO 4
<211> LENGTH: 23
<212> TYPE: DNA
<213> ORGANISM: Artificial Sequence
<220> FEATURE:
<223> OTHER INFORMATION: Synthesized nucleic acid molecule

<400> SEQUENCE: 4
tggtgcaagc ttaatacgac tca                                               23

<210> SEQ ID NO 5
<211> LENGTH: 11
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.
      "h" stands for a, c or u.

<400> SEQUENCE: 5
nnnnuhnnnn n                                                            11

<210> SEQ ID NO 6
<211> LENGTH: 28
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.

<400> SEQUENCE: 6
nnnnncugan gagnnnnnnc gaaannnn                                          28

<210> SEQ ID NO 7
<211> LENGTH: 47
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.

<400> SEQUENCE: 7
agaucgucnn nngucuaauc cucugaugag cgcaagcgaa acgaucu                     47

<210> SEQ ID NO 8
<211> LENGTH: 51
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.

<400> SEQUENCE: 8
agaucaugag gagucuaauc cunnnnnnnn nnnnnnnnnn nnnaugauc u                 51

<210> SEQ ID NO 9
<211> LENGTH: 72
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.

<400> SEQUENCE: 9
gggagacugu cuagaucaug aggagucuaa uccunnnnnn nnnnnnnnnn nnnnnnauga     60
ucugcaggau cc                                                         72

<210> SEQ ID NO 10
<211> LENGTH: 18
<212> TYPE: RNA
<213> ORGANISM: Artificial Sequence
<220> FEATURE:
<223> OTHER INFORMATION: Synthesized nucleic acid molecule

<400> SEQUENCE: 10
cugaugagcg caagcgaa                                                   18

<210> SEQ ID NO 11
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 11
ggaaucagcc ugacaccggc cc                                              22

<210> SEQ ID NO 12
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 12
ggcauccccg gcauggugcg cg                                              22

<210> SEQ ID NO 13
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 13
agcauuaccc ggcuggugcg cg                                              22

<210> SEQ ID NO 14
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 14
gcaucacggg gcaaucugcg cg                                              22

<210> SEQ ID NO 15
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 15
agcaucaccc ggauggugcg cg                                              22

<210> SEQ ID NO 16
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 16
agcaucaccc ggcuggugcg cg                                              22

<210> SEQ ID NO 17
<211> LENGTH: 22
<212> TYPE: RNA
<213> ORGANISM: Artificial Sequence
<220> FEATURE:
<223> OTHER INFORMATION: Synthesized nucleic acid molecule

<400> SEQUENCE: 17
agcguccacg gcaucgagcg cg                                              22

<210> SEQ ID NO 18
<211> LENGTH: 21
<212> TYPE: RNA
<213> ORGANISM: Artificial Sequence
<220> FEATURE:
<223> OTHER INFORMATION: Synthesized nucleic acid molecule

<400> SEQUENCE: 18
ugauggcuug cacuaagcgc g                                               21

<210> SEQ ID NO 19
<211> LENGTH: 21
<212> TYPE: RNA
<213> ORGANISM: Artificial Sequence
<220> FEATURE:
<223> OTHER INFORMATION: Synthesized nucleic acid molecule

<400> SEQUENCE: 19
ugauggcaug cacuaugcgc g                                               21

<210> SEQ ID NO 20
<211> LENGTH: 21
<212> TYPE: RNA
<213> ORGANISM: Artificial Sequence
<220> FEATURE:
<223> OTHER INFORMATION: Synthesized nucleic acid molecule

<400> SEQUENCE: 20
ugauggcaug caggaugcgc g                                               21

<210> SEQ ID NO 21
<211> LENGTH: 21
<212> TYPE: RNA
<213> ORGANISM: Artificial Sequence
<220> FEATURE:
<223> OTHER INFORMATION: Synthesized nucleic acid molecule

<400> SEQUENCE: 21
ugauggcaug caccaugcgc g                                               21

<210> SEQ ID NO 22
<211> LENGTH: 21

```
<212> TYPE: RNA
<213> ORGANISM: Artificial Sequence
<220> FEATURE:
<223> OTHER INFORMATION: Synthesized nucleic acid molecule

<400> SEQUENCE: 22
ugaugggaug caccaugcgc g                                              21

<210> SEQ ID NO 23
<211> LENGTH: 21
<212> TYPE: RNA
<213> ORGANISM: Artificial Sequence
<220> FEATURE:
<223> OTHER INFORMATION: Synthesized nucleic acid molecule

<400> SEQUENCE: 23
ugggccgauc gcaagggcgc g                                              21

<210> SEQ ID NO 24
<211> LENGTH: 75
<212> TYPE: RNA
<213> ORGANISM: Artificial Sequence
<220> FEATURE:
<223> OTHER INFORMATION: Cloned nucleic acid molecule

<400> SEQUENCE: 24
gggagacugu cuagaucaug aggaugcuaa uccuugaugg caugcacuau gcgcgaugau     60
cugcaggauc cgaga                                                     75

<210> SEQ ID NO 25
<211> LENGTH: 16
<212> TYPE: RNA
<213> ORGANISM: Artificial Sequence
<220> FEATURE:
<223> OTHER INFORMATION: Synthesized nucleic acid molecule

<400> SEQUENCE: 25
ugcagaucau gaggau                                                    16

<210> SEQ ID NO 26
<211> LENGTH: 36
<212> TYPE: RNA
<213> ORGANISM: Artificial Sequence
<220> FEATURE:
<223> OTHER INFORMATION: Cloned nucleic acid molecule

<400> SEQUENCE: 26
auccuugaug gcaugcacua ugcgcgauga ucugca                              36

<210> SEQ ID NO 27
<211> LENGTH: 16
<212> TYPE: RNA
<213> ORGANISM: Artificial Sequence
<220> FEATURE:
<223> OTHER INFORMATION: Synthesized nucleic acid molecule

<400> SEQUENCE: 27
ucagcgucau gaggau                                                    16

<210> SEQ ID NO 28
<211> LENGTH: 35
<212> TYPE: RNA
<213> ORGANISM: Artificial Sequence
<220> FEATURE:
<223> OTHER INFORMATION: Synthesized nucleic acid molecule
```

-continued

<210> SEQ ID NO 28

<400> SEQUENCE: 28
auccuugaug gggggguuagg gcgcgaugac gcuga                            35

<210> SEQ ID NO 29
<211> LENGTH: 16
<212> TYPE: RNA
<213> ORGANISM: Artificial Sequence
<220> FEATURE:
<223> OTHER INFORMATION: Synthesized nucleic acid molecule

<400> SEQUENCE: 29
ucagcgucau gaggau                                                 16

<210> SEQ ID NO 30
<211> LENGTH: 36
<212> TYPE: RNA
<213> ORGANISM: Artificial Sequence
<220> FEATURE:
<223> OTHER INFORMATION: Synthesized nucleic acid molecule

<400> SEQUENCE: 30
auccuugaug gcaugcacua ugcgcgauga cgcuga                           36

<210> SEQ ID NO 31
<211> LENGTH: 9
<212> TYPE: RNA
<213> ORGANISM: Artificial Sequence
<220> FEATURE:
<223> OTHER INFORMATION: Synthesized nucleic acid molecule

<400> SEQUENCE: 31 ucaugaggg                                                          9

<210> SEQ ID NO 32
<211> LENGTH: 29
<212> TYPE: RNA
<213> ORGANISM: Artificial Sequence
<220> FEATURE:
<223> OTHER INFORMATION: Synthesized nucleic acid molecule

<400> SEQUENCE: 32
cccuugaugg caugcacuau gcgcgauga                                   29

<210> SEQ ID NO 33
<211> LENGTH: 16
<212> TYPE: RNA
<213> ORGANISM: Artificial Sequence
<220> FEATURE:
<223> OTHER INFORMATION: Synthesized nucleic acid molecule

<400> SEQUENCE: 33
ucagcgucau gaggau                                                 16

<210> SEQ ID NO 34
<211> LENGTH: 35
<212> TYPE: RNA
<213> ORGANISM: Artificial Sequence
<220> FEATURE:
<223> OTHER INFORMATION: Synthesized nucleic acid molecule

<400> SEQUENCE: 34
auccuugaug gcccguuagg gcgcgaugac gcuga                            35

<210> SEQ ID NO 35
<211> LENGTH: 16

-continued

```
<212> TYPE: RNA
<213> ORGANISM: Artificial Sequence
<220> FEATURE:
<223> OTHER INFORMATION: Synthesized nucleic acid molecule

<400> SEQUENCE: 35
ucagcgucau gaggau                                                    16

<210> SEQ ID NO 36
<211> LENGTH: 35
<212> TYPE: RNA
<213> ORGANISM: Artificial Sequence
<220> FEATURE:
<223> OTHER INFORMATION: Synthesized nucleic acid molecule

<400> SEQUENCE: 36
auccuugaug gcccguuagg gcgcgaugac gcuga                               35

<210> SEQ ID NO 37
<211> LENGTH: 16
<212> TYPE: RNA
<213> ORGANISM: Artificial Sequence
<220> FEATURE:
<223> OTHER INFORMATION: Synthesized nucleic acid molecule

<400> SEQUENCE: 37
ucagcgucau gaggau                                                    16

<210> SEQ ID NO 38
<211> LENGTH: 35
<212> TYPE: RNA
<213> ORGANISM: Artificial Sequence
<220> FEATURE:
<223> OTHER INFORMATION: Synthesized nucleic acid molecule

<400> SEQUENCE: 38
auccuugaug gcccguuagg gcgcgaugac gcuga                               35
```

NUCLEIC ACID CATALYSTS WITH ENDONUCLEASE ACTIVITY

This Application claims the benefit of Fritz Eckstein, et al., U.S Provisional Application Ser. No. 60/059,473, entitled "Nucleic Acid Catalysts With Endonuclease Activity", filed Sep. 22, 1997. This application is hereby incorporated herein by reference in its entirety, including any drawings and figures.

BACKGROUND OF THE INVENTION

This invention relates to nucleic acid molecules with catalytic activity and derivatives thereof.

The following is a brief description of enzymatic nucleic acid molecules. This summary is not meant to be complete but is provided only for understanding of the invention that follows. This summary is not an admission that all of the work described below is prior art to the claimed invention.

Enzymatic nucleic acid molecules (ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, Nature 429 1986; Cech, 260 JAMA 3030, 1988; and Jefferies et al., 17 Nucleic Acids Research 1371, 1989).

Because of their sequence-specificity, trans-cleaving enzymatic nucleic acid molecules show promise as therapeutic agents for human disease (Usman & McSwiggen, 1995 Ann. Rep. Med. Chem. 30, 285–294; Christoffersen and Marr, 1995 J. Med. Chem. 38, 2023–2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

There are seven basic varieties of naturally-occurring enzymatic RNAs. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

In addition, several in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83–87; Beaudry et al., 1992, Science 257, 635–641; Joyce, 1992, Scientific American 267, 90–97; Breaker et al., 1994, TIBTECH 12, 268; Bartel et al., 1993, Science 261:1411–1418; Szostak, 1993, TIBS 17, 89–93; Kumar et al., 1995, FASEB J., 9, 1183; Breaker, 1996, Curr. Op. Biotech., 7, 442).

The enzymatic nature of a ribozyme is advantageous over other technologies, since the effective concentration of ribozyme necessary to effect a therapeutic treatment is generally lower than that of an antisense oligonucleotide. This advantage reflects the ability of the ribozyme to act enzymatically. Thus, a single ribozyme (enzymatic nucleic acid) molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

The development of ribozymes that are optimal for catalytic activity would contribute significantly to any strategy that employs RNA-cleaving ribozymes for the purpose of regulating gene expression. The hammerhead ribozyme functions with a 30 catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) can be 10- to 100-fold slower. In contrast, the RNase P holoenzyme can catalyze pre-tRNA cleavage with a $k_{cat}$ of ~30 min$^{-1}$ under optimal assay conditions. An artificial 'RNA ligase' ribozyme has been shown to catalyze the corresponding self-modification reaction with a rate of ~100 min$^{-1}$. In addition, it is known that certain modified hammerhead ribozymes that have substrate binding arms made of DNA catalyze RNA cleavage with multiple turnover rates that approach 100 min$^{-1}$. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain self-cleaving ribozymes may not be optimized to give maximal catalytic activity, or that entirely new RNA motifs could be made that display significantly faster rates for RNA phosphoester cleavage.

An extensive array of site-directed mutagenesis studies have been conducted with the hammerhead ribozyme to probe relationships between nucleotide sequence and catalytic activity. These systematic studies have made clear that most nucleotides in the conserved core of the hammerhead ribozyme cannot be mutated without significant loss of catalytic activity. In contrast, a combinatorial strategy that simultaneously screens- a large pool of mutagenized ribozymes for RNAs that retain catalytic activity could be used more efficiently to define immutable sequences and to identify new ribozyme variants. Although similar in vitro selection experiments have been conducted with the hammerhead ribozyme (Nakamaye & Eckstein, 1994, Biochemistry 33, 1271; Long & Uhlenbeck, 1994, Proc. Natl. Acad. Sci., 91, 6977; Ishizaka et al., 1995, BBRC 214, 403; Vaish et al., 1997, Biochemistry 36, 6495), none of these efforts have successfully screened full-sized hammerhead ribozymes for all possible combinations of sequence variants that encompass the entire catalytic core.

The hammerhead ribozyme is one of the smallest ribozymes known and has thus attracted much attention for the study of structure-function relationships in catalytic RNAs as well as for its potential for the sequence-specific inhibition of gene expression (Usman et al., supra). The hammerhead cleaves RNA sequence-specifically adjacent to the general triplet sequence NUX, where N is any nucleotide and X can be A, U or C. Cleavage behind a guanosine such as in GUG is very slow ($4.3 \times 10^{-5}$ min$^{-1}$) compared to the triplet substrate GUC (1 min$^{-1}$) (Baidya et al., 1997, *Biochemistry* 36, 1108). Although the X-ray structure of this ribozyme has been solved and a mechanism proposed (Pley et al., 1994 *Nature*, 372, 68; Scott et al., 1996, *Science* 274, 2065), the question of what determines its specificity for the NUX sequence is still largely unresolved. One way of obtaining an insight into this problem might be to compare sequences of hammerhead ribozymes with different triplet cleaving specificities. In previous publications it was demonstrated, by in vitro selection, that the native hammerhead sequence to cleave typical cleavage triplet, NUX, can not be altered (Nakamaye & Eckstein, 1994, *Biochemistry* 33, 1271; Long & Uhlenbeck, 1994, *Proc. Natl. Acad. Sci.,* 91, 6977; Ishizaka et al., 1995, *BBRC* 214, 403; Vaish et al., 1997, *Biochemistry* 36, 6495).

Tang et al., 1997, *RNA* 3, 914, reported novel ribozyme sequences with endonuclease activity, where the authors used an in vitro selection approach to isolate these ribozymes.

The references cited above are distinct from the presently claimed invention since they do not disclose and/or contemplate the catalytic nucleic acid molecules of the instant invention.

SUMMARY OF THE INVENTION

This invention relates to novel nucleic acid molecules with catalytic activity, which are particularly useful for cleavage of RNA or DNA. The nucleic acid catalysts of the instant invention are distinct from other nucleic acid catalysts known in the art. The nucleic acid catalysts of the instant invention do not share sequence homology with other known ribozymes. Specifically, nucleic acid catalysts of the instant invention are capable of catalyzing an intermolecular or intramolecular endonuclease reaction.

In a preferred embodiment, the invention features a nucleic acid molecule with catalytic activity having one of the formulae I–III:

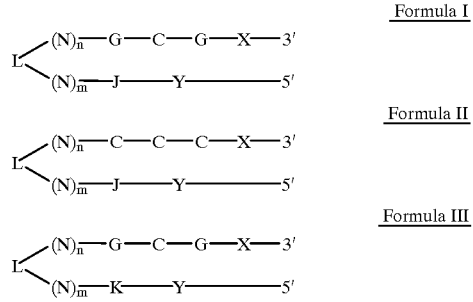

In each of the above formula, N represents independently a nucleotide or a non-nucleotide linker, which may be same or different; X and Y are independently oligonucleotides of length sufficient to stably interact (e.g., by forming hydrogen bonds with complementary nucleotides in the target) with a target nucleic acid molecule (the target can be an RNA, DNA or RNA/DNA mixed polymers); m and n are integers independently greater than or equal to 1 and preferably less than about 100, wherein if $(N)_m$ and $(N)_n$ are nucleotides, (N)m and (N)n are optionally able to interact by hydrogen bond interaction; J is an oligonucleotide of length 7 nucleotides; K is an oligonucleotide of length 6 nucleotides; L is a linker which may be present or absent (ie., the molecule is assembled from two separate molecules), but when present, is a nucleotide and/or a non-nucleotide linker, which may be a single-stranded and/or double-stranded region; and _ represents a chemical linkage (e.g. a phosphate ester linkage, amide linkage or others known in the art). C and G represent cytidine and guanosine nucleotides, respectively. The nucleotides in the each of the formula I–III are unmodified or modified at the sugar, base, and/or phosphate as known in the art.

In a preferred embodiment, the invention features nucleic acid molecules of Formula I, where the sequence of oligonucleotide J is selected from the group comprising 5'-GGCAUCC-3', 5'-AGCAUU-3', 5'-GCAUCA-3', 5'-AGCAUC-3', and. 5'-AGCGUC-3'.

In another preferred embodiment, the invention features nucleic acid molecules of Formula II, where the sequence of oligonucleotide J is 5'-GGAAUC-3'.

In a further preferred embodiment, the invention features nucleic acid molecules of Formula III, where the sequence of oligonucleotide K is selected from the group comprising 5'-UGAUG-3', 5'-UGAUC-3', and 5'-UGGGC-3'.

In yet another embodiment, the nucleotide linker (L) is a nucleic acid aptamer, such as an ATP aptamer, HIV Rev aptamer (RRE), HIV Tat aptamer (TAR) and others (for a review see Gold et al., 1995, *Annu. Rev. Biochem.,* 64, 763; and Szostak & Ellington, 1993, in *The RNA World,* ed. Gesteland and Atkins, pp 511, CSH Laboratory Press). A "nucleic acid aptamer" as used herein is meant to indicate nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

In yet another embodiment, the non-nucleotide linker (L) is as defined herein. The term "non-nucleotide" as used herein include either abasic nucleotide, polyether, polyamine, polyamide, peptide, carbohydrate, lipid, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. Thus, in a preferred embodiment, the invention features an enzymatic nucleic acid molecule having one or more non-nucleotide moieties, and having enzymatic activity to cleave an RNA or DNA molecule. By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. The terms "abasic" or "abasic nucleotide" as used herein encompass sugar moieties lacking a base or having other chemical groups in place of base at the 1' position.

In preferred embodiments, the enzymatic nucleic acid includes one or more stretches of RNA, which provide the enzymatic activity of the molecule, linked to the non-nucleotide moiety. The necessary RNA components are known in the art (see for e.g., Usman et al., supra). By RNA is meant a molecule comprising at least one ribonucleotide residue.

Thus, in one preferred embodiment, the invention features ribozymes that inhibit gene expression and/or cell proliferation. These chemically or enzymatically synthesized nucleic acid molecules contain substrate binding domains that bind to accessible regions of specific target nucleic acid molecules. The nucleic acid molecules also contain domains that catalyze the cleavage of target. Upon binding, the enzymatic nucleic acid molecules cleave the target molecules, preventing for example, translation and protein accumulation. In the absence of the expression of the target gene, cell proliferation, for example, is inhibited.

In another aspect of the invention, enzymatic nucleic acid molecules that cleave target molecules are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review see Couture and Stinchcomb, 1996, *TIG.*, 12, 510).

In a preferred embodiment, an expression vector comprising nucleic acid sequence encoding at least one of the nucleic acid catalyst of the instant invention is disclosed. The nucleic acid sequence encoding the nucleic acid catalyst of the instant invention is operable linked in a manner which allows expression of that nucleic acid molecule.

In one embodiment, the expression vector comprises: a transcription initiation region (e.g., eukaryotic pol I, II or III initiation region); b) a transcription termination region (e.g., eukaryotic pol I, II or III termination region); c) a gene encoding at least one of the nucleic acid catalyst of the instant invention; and wherein said gene is operably linked to said initiation region and said termination region, in a manner which allows expression and/or delivery of said nucleic acid molecule. The vector may optionally include an open reading frame (ORF) for a protein operably linked on the 5' side or the 3'-side of the gene encoding the nucleic acid catalyst of the invention; and/or an intron (intervening sequences).

By "patient" is meant an organism which is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells.

By "vectors" is meant any nucleic acid- and/or viral-based technique used to deliver a desired nucleic acid.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol*, 217,47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad Sci. USA*, 89, 10802–6; Chen et al., 1992 *Nucleic Acids Res.*, 20, 4581–9; Yu et al., 1993 *Proc. Natl. Acad Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4; Thompson et al., 1995 *Nucleic Acids Res.* 23, 2259; Sullenger & Cech, 1993, *Science*, 262, 1566). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In a preferred embodiment, the invention features a method of synthesis of enzymatic nucleic acid molecules of instant invention which follows the procedure for normal chemical synthesis of RNA as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 µmol scale protocol with a 5 min coupling step for alkylsilyl protected nucleotides and 2.5 min coupling step for 2'-O-methylated nucleotides. Table I outlines the amounts, and the contact times, of the reagents used in the synthesis cycle. A 6.5-fold excess (163 µL of 0.1M=16.3 µmol) of phosphoramidite and a 24-fold excess of S-ethyl tetrazole (238 µL of 0.25M=59.5 µmol) relative to polymer-bound 5'-hydroxyl is used in each coupling cycle. Average coupling yields on the 394 Applied Biosystems, Inc. synthesizer, determined by colorimetric quantitation of the trityl fractions, is 97.5–99%. Other oligonucleotide synthesis reagents for the 394 Applied Biosystems, Inc. synthesizer-:detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile is used directly from the reagent bottle. S-Ethyl tetrazole solution (0.25M in acetonitrile) is made up from the solid obtained from American International Chemical, Inc.

In a preferred embodiment, deprotection of the chemically synthesized nucleic acid catalysts of the invention is performed as follows. The polymer-bound oligoribonucleotide, trityl-off, is transferred from the synthesis column to a 4 mL glass screw top vial and suspended in a solution of methylamine (MA) at 65° C. for 10 min. After cooling to −20° C., the supernatant is removed from the polymer support. The support is washed three times with 1.0 mL of EtOH:MeCN:H$_2$O/3:1:1, vortexed and the supernatant is then added to the first supernatant. The combined supernatants, containing the oligoribonucleotide, are dried to a white powder.

The base-deprotected oligoribonucleotide is resuspended in anhydrous TEA·HF/NMP solution (250 μL of a solution of 1.5 mL N-methylpyrrolidinone, 750 μL TEA and 1.0 mL TEA·3HF to provide a 1.4M HF concentration) and heated to 65° C. for 1.5 h. The resulting, fully deprotected, oligomer is quenched with 50 mM TEAB (9 mL) prior to anion exchange desalting.

For anion exchange desalting of the deprotected oligomer, the TEAB solution is loaded on to a Qiagen 500® anion exchange cartridge (Qiagen Inc.) that is prewashed with 50 mM TEAB (10 mL). After washing the loaded cartridge with 50 mM TEAB (10 mL), the RNA is eluted with 2M TEAB (10 mL) and dried down to a white powder. The average stepwise coupling yields are generally >98% (Wincott et al., 1995 *Nucleic Acids Res.* 23,2677–2684).

Ribozymes of the instant invention are also synthesized from DNA templates using bacteriophage T7 RNA polymerase (Milligan and Uhlenbeck, 1989, *Methods Enzymol.* 180, 51).

Ribozymes are purified by gel electrophoresis using general methods or are purified by high pressure liquid chromatography (HPLC; See Wincott et al., supra) the totality of which is hereby incorporated herein by reference) and are resuspended in water.

In another preferred embodiment, catalytic activity of the molecules described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci* 17, 334; Usman et al., International Publication No. WO 93/15187; and Rossi et al., International Publication No. WO 91/03162; Sproat, U.S. Pat. No. 5,334, 711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein.).

By "enhanced enzymatic activity" is meant to include activity measured in cells and/or in vivo where the activity is a reflection of both catalytic activity and ribozyme stability. In this invention, the product of these properties is increased or not significantly (less that 10 fold) decreased in vivo compared to an all RNA ribozyme.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, *Biochemistry,* 35, 14090). Such ribozymes herein are said to "maintain" the enzymatic activity on all RNA ribozyme.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIGS. 1A–1C, is a diagrammatic representation of the hammerhead ribozyme SEQ ID NO: 6 domain and target SEQ ID NO: 5 known in the art. Stem II can be ≧2 base-pair long. Each N is independently any base or non-nucleotide as used herein; 1B is a diagrammatic representation of a self-cleaving hammerhead ribozyme, SEQ ID NO: 7, 1C is a diagrammatic representation of a random pool of self-cleaving RNA SEQ ID NO: 8. N indicates the region with random nucleotides.

FIG. 2 is a schematic representation of a non-limiting in vitro selection strategy used to evolve nucleic acid catalysts.

FIG. 3 shows sequences of individual RNAs that represent new classes of self-cleaving ribozymes SEQ ID NO: 9–23. Also shown are rates of catalysis ($k_{in\text{-}cis}$ (min$^{-1}$)) for each of the new self-cleaving RNA sequences. The underlined sequences indicate the regions capable of interacting with each other.

FIG. 4 summarizes structure mapping studies on clone 40 RNA SEQ ID NO: 24.

NUCLEIC ACID CATALYSTS

Figure 1:
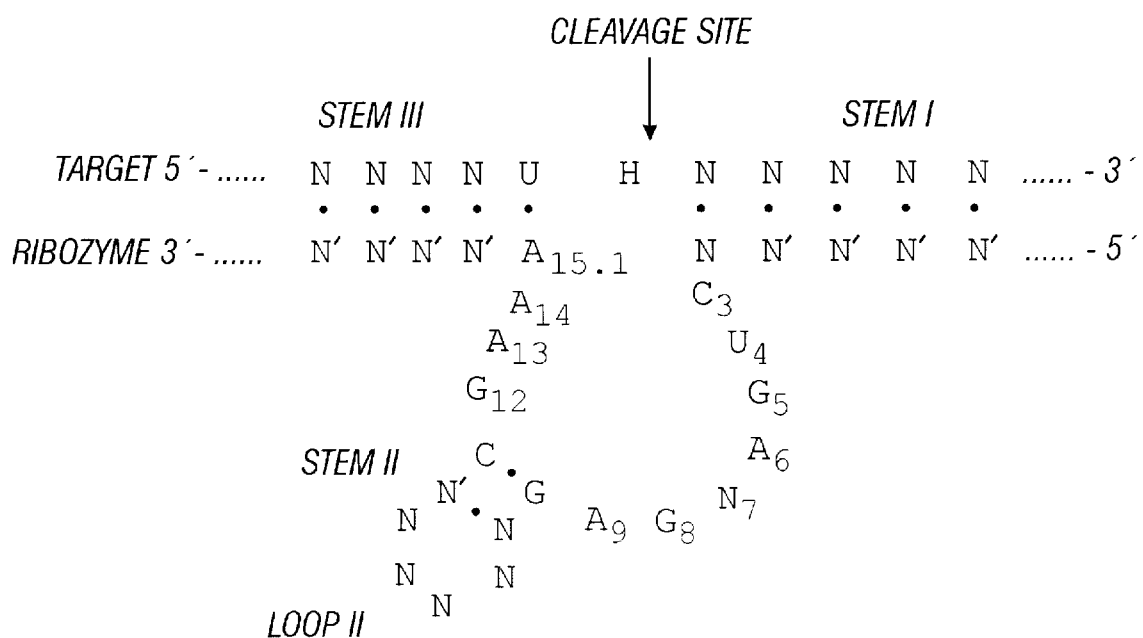
Figure 1B:
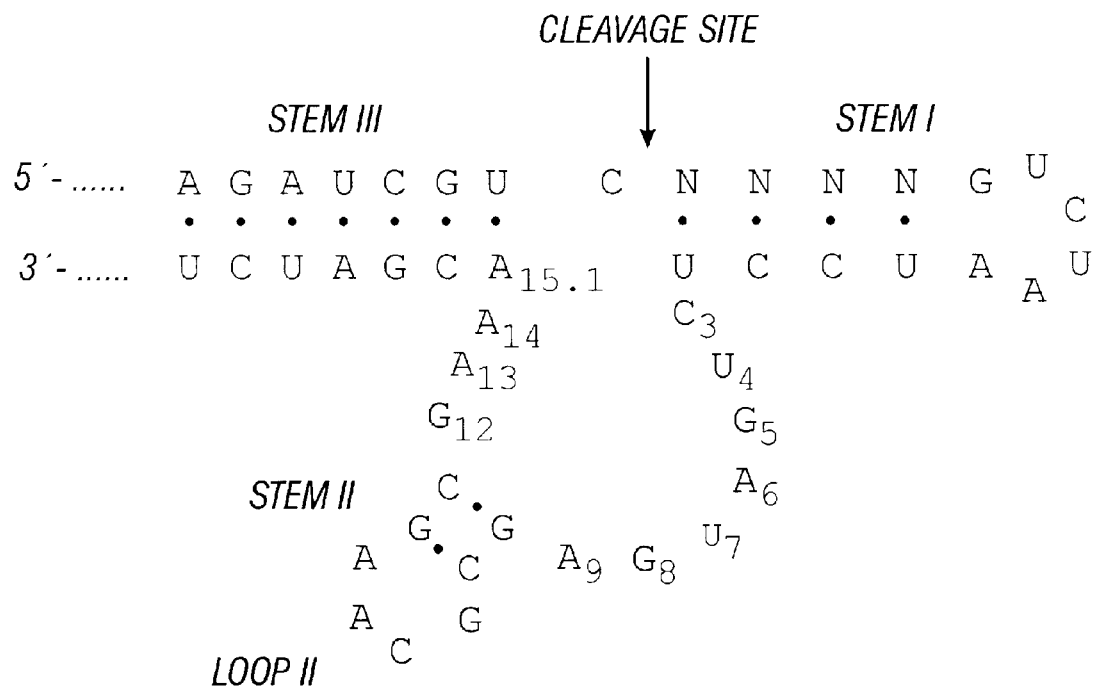
Figure 1C:
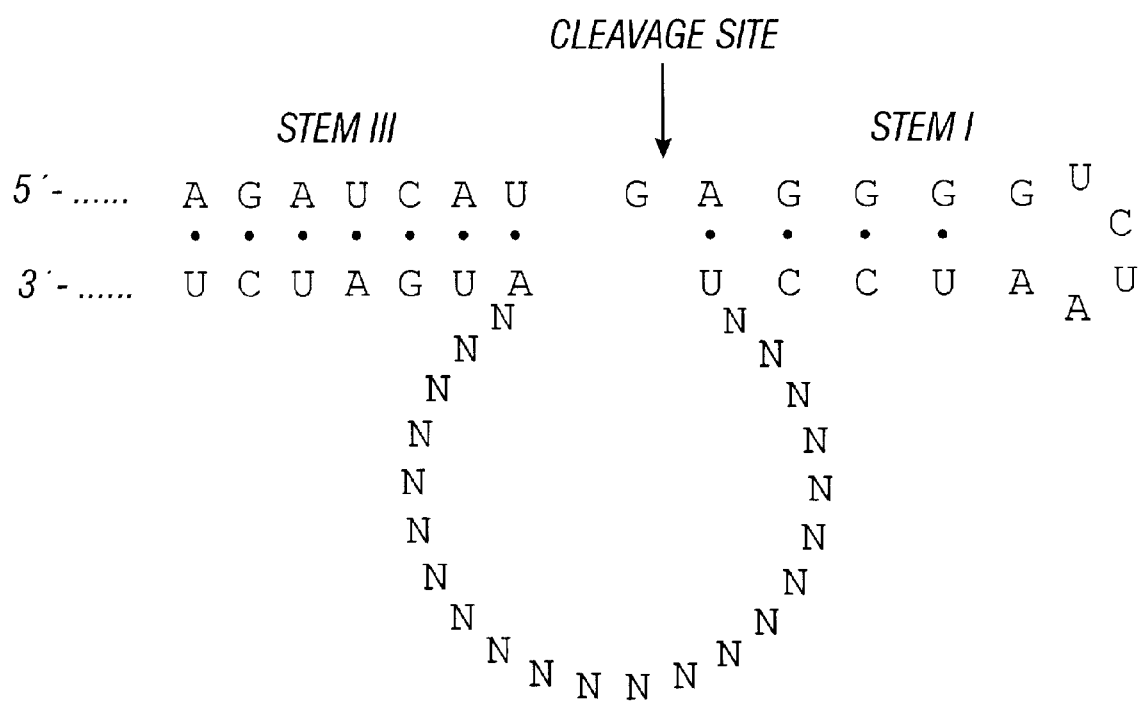
Figure 2:
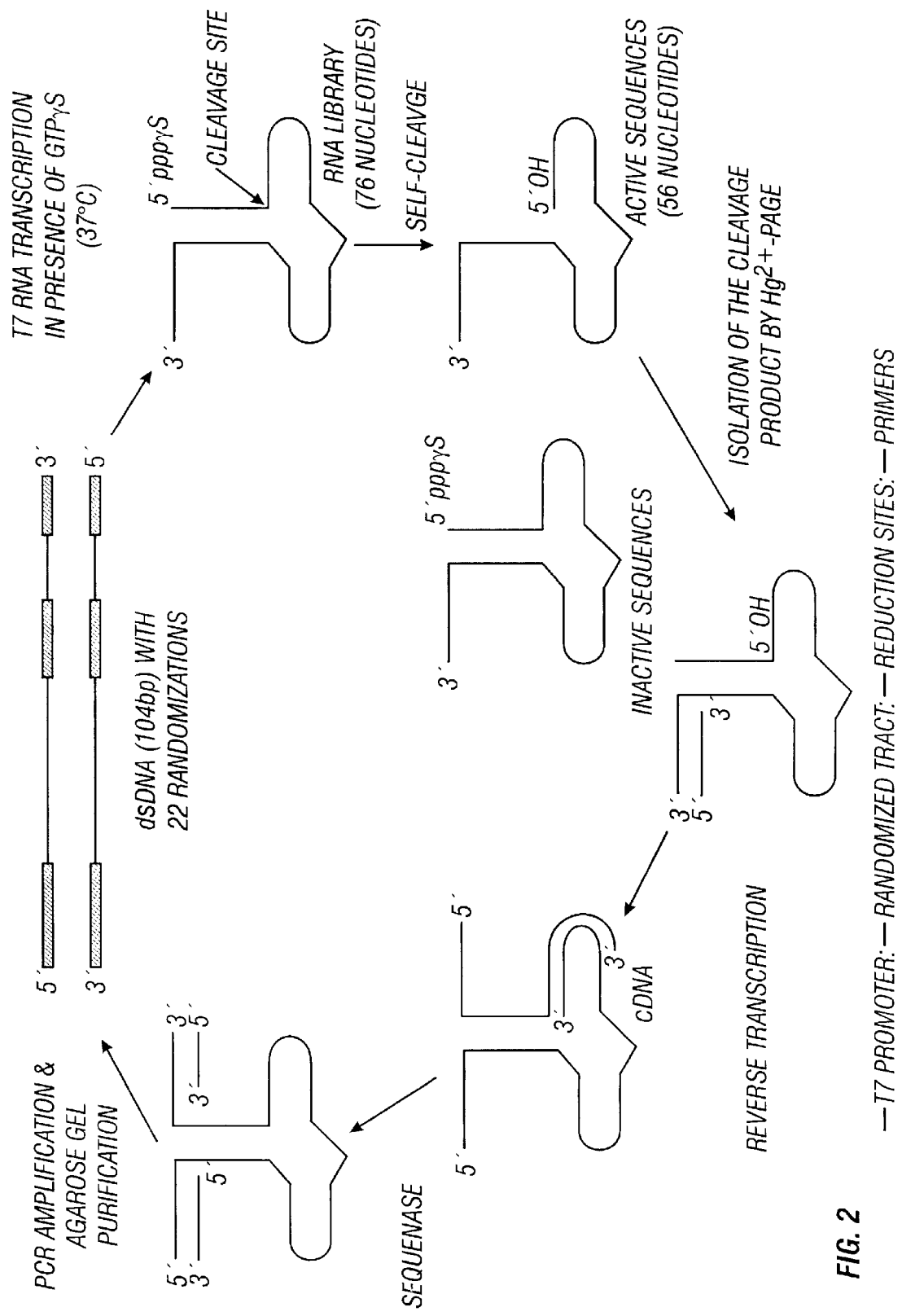

The invention provides nucleic acid catalysts and methods for producing a class of enzymatic nucleic acid cleaving agents which exhibit a high degree of specificity for the nucleic acid sequence of a desired target. The enzymatic nucleic acid molecule is preferably targeted to a highly conserved sequence region of a target such that specific diagnosis and/or treatment of a disease or condition in a variety of biological system can be provided with a single enzymatic nucleic acid. Such enzymatic nucleic acid molecules can be delivered exogenously to specific cells as required. In the preferred hammerhead motif the small size (less than 60 nucleotides, preferably between 30–40 nucleotides in length) of the molecule allows the cost of treatment to be reduced.

By the phrase "nucleic acid catalyst" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region (e.g. X and Y in formulae I–III) to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, nucleozyme, DNAzyme, RNA enzyme, endoribonuclease, endonuclease, minizyme, leadzyme, oligozyme or DNA enzyme. All of these terminologies describe nucleic acid molecules with enzymatic activity.

By "nucleic acid molecule" as used herein is meant a molecule comprising nucleotides. The nucleic acid can be composed of modified or unmodified nucleotides or non-nucleotides or various mixtures and combinations thereof.

By "complementarity" is meant a nucleic acid that can form hydrogen bond(s) with other RNA sequence by either traditional Watson-Crick or other non-traditional types (for example, Hoogsteen type) of base-paired interactions.

By "oligonucleotide" as used herein, is meant a molecule comprising two or more nucleotides.

The specific enzymatic nucleic acid molecules described in the instant application are not limiting in the invention and those skilled in the art will recognize that all that is important in an enzymatic nucleic acid molecule of this invention is that it has a specific substrate binding site (e.g., X and Y of Formulae I–III above) which is complementary to one or more of the target nucleic acid regions, and that it have nucleotide sequences within or surrounding that substrate binding site which impart a nucleic acid cleaving activity to the molecule.

By "enzymatic portion" is meant that part of the ribozyme essential for cleavage of an RNA substrate.

By "substrate binding arm" or "substrate binding domain" is meant that portion of a ribozyme which is complementary to (i.e., able to base-pair with) a portion of its substrate. Generally, such complementarity is 100%, but can be less if desired. For example, as few as 10 nucleotides out of a total of 14 may be base-paired. Such arms are shown generally in FIG. 1A and as X and Y in Formulae I–III. That is, these arms contain sequences within a ribozyme which are intended to bring ribozyme and target RNA together through complementary base-pairing interactions. The ribozyme of the invention may have binding arms that are contiguous or non-contiguous and may be of varying lengths. The length of the binding arm(s) are preferably greater than or equal to four nucleotides; specifically 12–100 nucleotides; more specifically 14–24 nucleotides long. The two binding arms are chosen, such that the length of the binding arms are symmetrical (ie., each of the binding arms is of the same length; e.g., five and five nucleotides, six and six nucleotides or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

Therapeutic ribozymes must remain stable within cells until translation of the target RNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes to enhance their nuclease stability. The term "nucleotide" is used as recognized in the art to include natural bases, and modified bases well known in the art. Such bases are generally located at the 1' position of a sugar moiety. Nucleotide generally comprise a base, sugar and a phosphate group. The nucleotides can be unmodified or modified at the sugar, phosphate and/or base moeity, (see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2, 4, 6-trimethoxy benzene, 3-methyluracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g 6-methyluridine) and others (Burgin et al., 1996, *Biochemistry,* 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

In particular, the invention features modified ribozymes having a base substitution selected from pyridin-4-one, pyridin-2-one, phenyl, pseudouracil, 2, 4, 6-trimethoxy benzene, 3-methyluracil, dihydrouracil, naphthyl, 6-methyluracil and aminophenyl.

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modification of enzymatic nucleic acid molecules have been extensively described in the art (see Eckstein et al., International Publication PCT No. WO 92/07065; Perrault et al. *Nature* 1990, 344, 565–568; Pieken et al. *Science* 1991, 253, 314–317; Usman and Cedergren, *Trends in Biochem. Sci* 1992, 17, 334–339; Usman et al. International Publication PCT No. WO 93/15187; Sproat, U.S. Pat. No. 5,334,711 and Beigelman et al., 1995 *J. Biol. Chem.* 270, 25702).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

As the term is used in this application, non-nucleotide-containing enzymatic nucleic acid means a nucleic acid molecule that contains at least one non-nucleotide component which replaces a portion of a ribozyme, e.g. but not limited to, a double-stranded stem, a single-stranded "catalytic core" sequence, a single-stranded loop or a single-stranded recognition sequence. These molecules are able to cleave (preferably, repeatedly cleave) separate RNA or DNA molecules in a nucleotide base sequence specific manner. Such molecules can also act to cleave intramolecularly if that is desired. Such enzymatic molecules can be targeted to virtually any RNA transcript.

Administration of Ribozymes

Sullivan et al., PCT WO 94/02595, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

The invention also features the use of the a composition comprising surface-modified liposomes containing poly (ethylene glycol) lipids (PEG-modified, or long-circulating liposomes or stealth liposomes). These formulations offer an method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwataet al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta,* 1238, 86–90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences,* Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. In a one aspect, the invention provides enzymatic nucleic acid molecules that can be delivered exogenously to specific cells as required. The enzymatic nucleic acid molecules are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. Using the methods described herein, other enzymatic nucleic acid molecules that cleave target nucleic acid may be derived and used as described above. Specific examples of nucleic acid catalysts of the instant invention are provided below in the Tables and figures.

Alternatively, the enzymatic nucleic acid molecules of the instant invention can be expressed within cells from eukaryotic promoters (e.g., Izant and Weintraub, 1985 *Science* 229, 345; McGarry and Lindquist, 1986 *Proc. Natl. Acad. Sci. USA* 83, 399; Scanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225; Thompson et al., 1995 *Nucleic Acids Res.* 23, 2259; Good et al., 1997, *Gene Therapy,* 4, 45; all of the references are hereby incorporated in their totality by reference herein). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO 93/23569, and Sullivan et al., PCT WO 94/02595; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856; all of the references are hereby incorporated in their totality by reference herein).

Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA,* 87, 6743–7; Gao and Huang 1993 *Nucleic Acids Res.,* 21, 2867–72; Lieber et al., 1993 *Methods Enzymol.,* 217, 47–66; Zhou et al., 1990 *Mol. Cell. Biol.,* 10, 4529–37). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad Sci. USA,* 89, 10802–6; Chen et al., 1992 *Nucleic Acids Res.,* 20, 4581–9; Yu et al., 1993 *Proc. Natl. Acad. Sci. USA,* 90, 6340–4; L'Huillier et al., 1992 *EMBO J.* 11, 4411–8; Lisziewicz et al., 1993 *Proc. Natl. Acad Sci. U.S.A.,* 90, 8000–4; Thompson et al., 1995 *Nucleic Acids Res.* 23, 2259; Sullenger & Cech, 1993, *Science,* 262, 1566). More specifically, transcription units such as the ones derived from genes encoding U6 small nuclear (snRNA), transfer RNA (tRNA) and adenovirus VA RNA are useful in generating high concentrations of desired RNA molecules such as ribozymes in cells (Thompson et al., supra; Couture and Stinchcomb, 1996, supra; Noonberg et al., 1994, *Nucleic Acid Res.,* 22, 2830; Noonberg et al., U.S. Pat. No. 5,624,803; Good et al., 1997, *Gene Ther.* 4, 45; Beigelman et al., International PCT Publication No. WO 96/18736; all of these publications are incorporated by reference herein. Examples of transcription units suitable for expression of ribozymes of the instant invention are shown in FIG. 15. The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In yet another aspect the invention features an expression vector comprising nucleic acid sequence encoding at least one of the catalytic nucleic acid molecule of the invention, in a manner which allows expression of that nucleic acid molecule. The expression vector comprises in one embodiment; a) a transcription initiation region; b) a transcription termination region; c) a gene encoding at least one said nucleic acid molecule; and wherein said gene is operably linked to said initiation region and said termination region, in a manner which allows expression and/or delivery of said nucleic acid molecule. In another preferred embodiment the expression vector comprises: a) a transcription initiation region; b) a transcription termination region; c) an open reading frame; d) a gene encoding at least one said nucleic acid molecule, wherein said gene is operably linked to the 3'-end of said open reading frame; and wherein said gene is operably linked to said initiation region, said open reading frame and said termination region, in a manner which allows expression and/or delivery of said nucleic acid molecule. In yet another embodiment the expression vector comprises: a) a transcription initiation region; b) a transcription termination region; c) an intron; d) a gene encoding at least one said nucleic acid molecule; and wherein said gene is operably linked to said initiation region, said intron and said termination region, in a manner which allows expression and/or delivery of said nucleic acid molecule. In another embodiment, the expression vector comprises: a) a transcription initiation region; b) a transcription termination region; c) an intron; d) an open reading frame; e) a gene encoding at least one said nucleic acid molecule, wherein said gene is operably linked to the 3'-end of said open reading frame; and wherein said gene is operably linked to said initiation region, said intron, said open reading frame and said termination region, in a manner which allows expression and/or delivery of said nucleic acid molecule.

By "consists essentially of" is meant that the active ribozyme contains an enzymatic center or core equivalent to those in the examples, and binding arms able to bind target nucleic acid molecules such that cleavage at the target site occurs. Other sequences may be present which do not interfere with such cleavage.

EXAMPLES

The following are non-limiting examples showing the selection, isolation, synthesis and activity of enzymatic nucleic acids of the instant invention.

An extensive array of site-directed mutagenesis studies have been conducted with the hammerhead to probe relationships between nucleotide sequence and catalytic activity. These systematic studies have made clear that most nucleotides in the conserved core of the hammerhead ribozyme (Forster & Symons, 1987, *Cell*, 49, 211) cannot be mutated without significant loss of catalytic activity. In contrast, a combinatorial strategy that simultaneously screens a large pool of mutagenized ribozymes for RNAs that retain catalytic activity could be used more efficiently to define immutable sequences and to identify new ribozyme variants (breaker, 1997, supra). For example, Joseph and Burke (1993; *J. Biol. Chem.*, 268, 24515) have used an in vitro selection approach to rapidly screen for sequence variants of the 'hairpin' self-cleaving RNA that show improved catalytic activity. This approach was successful in identifying two mutations in the hairpin ribozyme that together give a 10-fold improvement in catalytic rate. Although similar in vitro selection experiments have been conducted with the hammerhead ribozyme (Nakamaye & Eckstein, 1994, supra; Long & Uhlenbeck, 1994, supra; Ishizaka et al., 1995, supra), none of these efforts have successfully screened full-sized hammerhead ribozymes for all possible combinations of sequence variants that encompass the entire catalytic core.

Applicant employed in vitro selection strategy to comprehensively test whether the natural consensus sequence for the core of the hammerhead ribozyme produces maximal catalytic rates, or whether sequence variants of this ribozyme could catalyze endonuclease reaction similar to or better than the hammerhead ribozyme.

The procedure reported herein to select for intramolecular AUG cleaving sequences is based on Applicant's previously reported selection of alternative GUC cleaving hammerhead sequences (Vaish et al., supra; incorporated by reference herein).

Example 1: In vitro selection of self-cleaving RNAs from a random pool

It was of interest to see what changes have to be imposed on the native hammerhead sequence for it to cleave after AUG, which usually resists cleavage, and thus arrive at a ribozyme with a new specificity. To achieve this, an in vitro selection was undertaken, where the number of randomized positions in the starting pool corresponded to the number of nucleotides typically found in the core and stem-loop II region of a hammerhead ribozyme. This would allow all possible sequence permutations to be explored in the search for a hammerhead which is able to cleave behind AUG (Robertson & Joyce, 1990; Ellington and Szostak, 1990; Tuerk & Gold, 1990; Wright & Joyce, 1997; Carmi et al., 1997; for reviews see Breaker, 1997; Abelson, 1996; Ellington, 1997; Chapman & Szostak, 1994).

An initial pool of dsDNAs containing 22 randomized positions flanked by two constant regions were synthesized. These were transcribed, with transcription being initiated with GTPγS, to produce a pool of potential ribozymes. Self-cleavage of active ribozymes occurs during transcription and the cleavage products can then be separated from intact transcripts by means of a mercury gel (Igloi, *Biochemistry* 27, 3842). The recovered cleavage products were then reverse transcribed and amplified by PCR to give a dsDNA pool of selected ribozymes. This selection procedure was repeated for 13 cycles before the dsDNA pool was cloned and sequenced.

Oligodeoxyribonucleotides and oligoribonucleotides were chemically synthesized and purified as previously described (Vaish et al., supra). Primers used in the selection:

```
Primer 1:
5'-TGGTGCAAGCTTAATACGACTCACTATAGGGAGACTGTCTAGATCATGA   SEQ ID NO:1.
   GGATGCTA-3'

Primer 2:
5'-TCTCGGATCCTGCAGATCATNNNNNNNNNNNNNNNNNNNNNNAGGATT    SEQ ID NO:2.
   AGCATCCTCAT-3'
```

These two primers were used for the initial Sequenase reaction, and Primer 2 also functioned as restoration primer for the reintroduction of the lost sequences during cleavage. Reverse transcription (RT)-Primer, 5'-TCTCGGATCCTGCAGATCAT-3' SEQ ID NO:3; and polymerase chain reaction (PCR)-Primer, 5'-TGGTGCAAGCTTAATACGACTCA-3' SEQ ID NO:4, with HindIII (5'-end) and BamHI and PstI (3'-end) sites in boldface; T7 promoter is underlined; ribozyme cleavage triplet in italics; N, randomized nucleotides. RNA selection was performed as described (Vaish et al., supra, incorporated by reference herein) with modifications to the initial two cycles of selection. Transcriptions from Pool 0 and Pool 1 were performed on a larger scale (10×500 µl and 1×250 µl, respectively) for 12 h and PCR amplification (Step 5) was omitted in each case. Successive transcriptions were performed at 100 µl volume. Transcription reactions were for decreasing periods of time from 12 h ($1^{st}$ cycle) to 1 min ($13^{th}$ cycle), where reactions for short periods were quenched by addition of EDTA (75 mM final conc.). All transcriptions were performed with 1 µM DNA. DNA template in the PCR mixture was at least $1\times10^{-15}$M. The minimum concentration of RNA template was $1\times10^{-8}$M for reverse transcription. The concentrations were determined assuming a molar extinction coefficient of 6600.

A selection pressure was exerted by progressively reducing the time of transcription from 12 h for the first six cycles, to 6 h for the seventh, 1 h for the eighth, 30 min for the ninth and tenth, 5 min for the eleventh, and 1 min for the twelve and thirteenth cycle. White colonies were selected randomly each from pools 7 and 10 and those showing self-cleavage upon transcription were sequenced. There was no homology among the sequences.

Cloning and sequencing was performed as described (Vaish et al., supra) except that the dsDNA was digested with HindIII and BamHI. Clones from pools seven and ten were tested for transcript self-cleavage from linearized plasmids. For clones from Pool 13 plasmid DNA was amplified by PCR, using the RT- and PCR-primers, and then transcribed. Rates of intramolecular cleavage of transcripts were determined as described but with 10 u of enzyme per µl. Active clones were sequenced. A transcript of only 50 nucleotides, without the extra sequences for cloning beyond stem III, showed a $k_{in-cis}$ of 0.32 min$^{-1}$.

By "randomized region" is meant a region of completely random sequence and/or partially random sequence. By completely random sequence is meant a sequence wherein theoretically there is equal representation of A, T, G and C nucleotides or modified derivatives thereof, at each position in the sequence. By partially random sequence is meant a sequence wherein there is an unequal representation of A, T, G and C nucleotides or modified derivatives thereof, at each position in the sequence. A partially random sequence can therefore have one or more positions of complete randomness and one or more positions with defined nucleotides.
Characterization of New self-cleaving ribozyme sequences The intramolecular cleavage rate of the most active sequence of pool 7 was 0.03 min$^{-1}$ and that of pool 10 was 0.06 min$^{-1}$ (FIG. 3). Seventy clones from pool thirteen were picked and amplified by PCR. Of these 20 gave full length DNA and were transcribed and of these 14 showed intramolecular cleavage. These 14 active ribozymes could be divided into two groups: one group contained transcripts with 22 nucleotides in the randomized region and the second group contained a deletion in this region with only 21 nucleotides being present. Several sequences were represented twice such as those of clones 29, 36 and 40. One of the most active sequences, from clone 13/40, with $k_{in\text{-}cis}$ of 0.52 min$^{-1}$ was chosen for further study. In comparison, under these conditions the intramolecular cleavage of the native hammerhead with a GUC triplet was $k_{in\text{-}cis}$ of 0.56 min$^{-1}$, indicating that the cleavage activity of the selected ribozyme, Rz13/40, with an AUG triplet is comparable.

In order to acquire some information on the secondary structure of Rz13/40 a limited nuclease digest of the 3'-end-labeled, full-length ribozyme was performed. Rz13/40 was prepared by transcription in such a way that cleavage was minimized and full-length ribozyme. A full length transcript for the intramolecularly cleaving ribozyme was generated by transcription at 12° C. for 8 h (Frank et al., 1996, *RNA*, 2, 1179; incorporated by reference herein) and 3'-end labeled with $^{32}$pCp. Limited nuclease digestions with RNase A, RNase T1 and nuclease S1 were performed as Hodson et al., 1994, *Nucleic Acids Res.*, 22, 1620; Loria et a., 1996, *RNA*, 2,551; both are incorporated by reference herein). Alkaline hydrolysis of labeled RNA was performed in 50 mM NaHCO$_3$ at 100° C. for 7.5 minutes.

Figure 4:
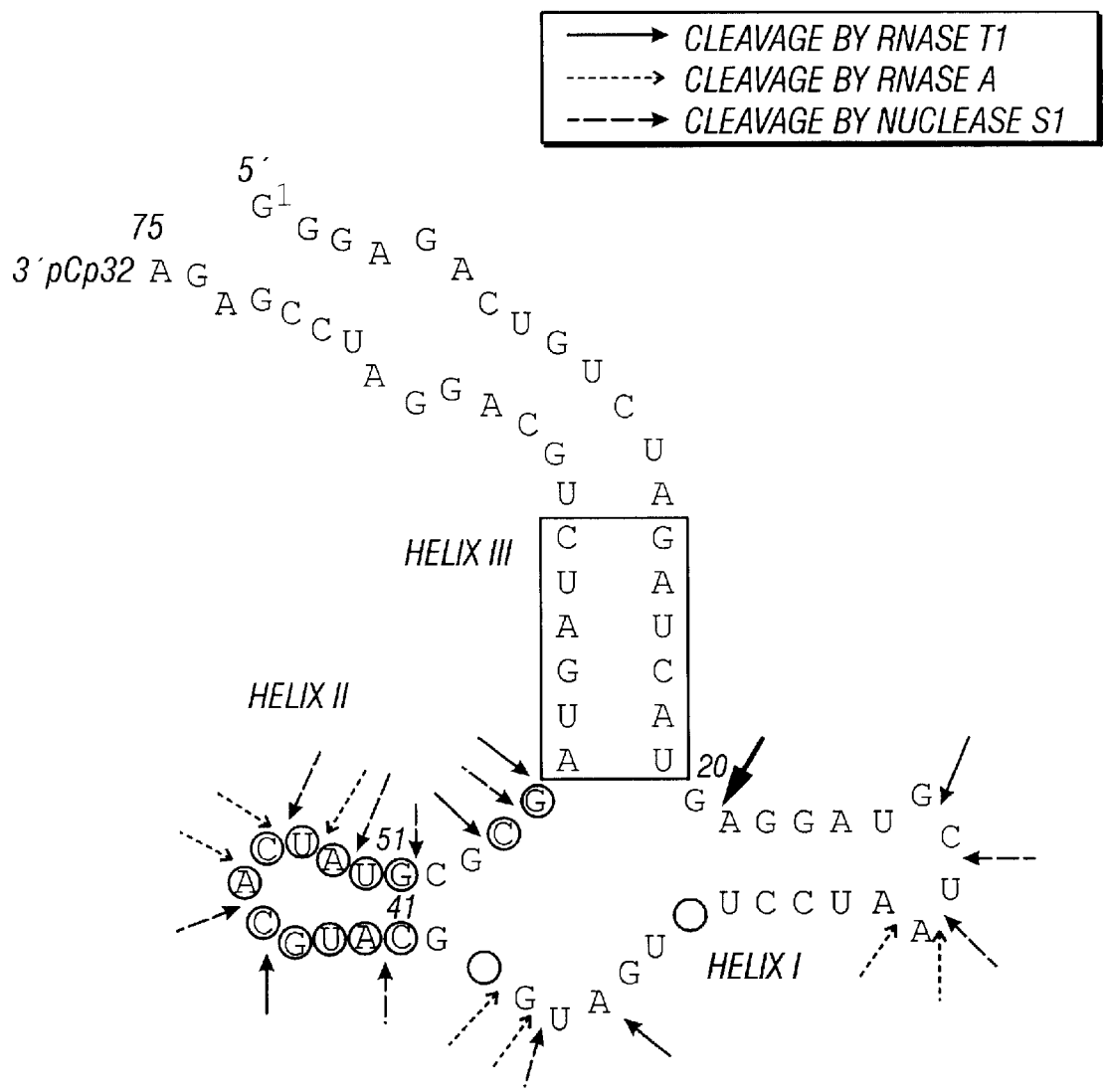

Limited digestion with RNase A and T1 and nuclease S1, which indicates single-stranded regions, gave a digestion pattern consistent with Rz13/40 adopting a hammerhead-type structure, which comprised three base-paired helices surrounding a single-stranded core (FIG. 4). Since the structure of Rz13/40 resembles the hammerhead structure, the same numbering system has been adopted, with positions 3 and 9 in the core being considered vacant.

The data of nuclease digestion corresponded fairly well with the MFOLD structure except for a few discrepancies. MFOLD shows base pairing in the core region between U$^7$ and G$^{14}$; G$^8$ and C$^{13}$; G$^{L2.1}$ and U$^{L2.5}$; and U$^4$ and G$^{17}$ although there is cleavage at these positions by the nucleases.
Ribozyme Engineering Sequence, chemical and structural variants of ribozymes of the present invention can be engineered using the techniques shown above and known in the art to cleave a separate target RNA or DNA in trans. For example, the size of ribozymes can, be reduced or increased using the techniques known in the art (Zaug et al., 1986, *Nature*, 324, 429; Ruffner et al., 1990, *Biochem.*, 29, 10695; Beaudry et al., 1990, *Biochem.*, 29, 6534; McCall et al., 1992, *Proc. Natl. Acad. Sci., USA.*, 89, 5710; Long et al., 1994, Supra; Hendry et al., 1994, *BBA* 1219, 405; Benseler et al., 1993, *JACS*, 115, 8483; Thompson et al., 1996, *Nucl. Acids Res.*, 24, 4401; Michels et al., 1995, *Biochem.*, 34, 2965; Been et al., 1992, *Biochem.*, 31, 11843; Guo et al., 1995, *EMBO. J.*, 14, 368; Pan et al., 1994, *Biochem.*, 33, 9561; Cech, 1992, *Curr. Op. Struc. Bio.*, 2, 605; Sugiyama et al., 1996, *FEBS Lett.*, 392, 215; Beigelman et al., 1994, *Bioorg. Med. Chem.*, 4, 1715; all are incorporated in its totality by reference herein). For example the stem-loop II domain of the ribozymes may not be essential for catalytic activity and hence could be systematically reduced in size using a variety of methods known in the art, to the extent that the overall catalytic activity of the ribozyme is not significantly decreased.

Further rounds of in vitro selection strategies described herein and variations thereof can be readily used by a person skilled in the art to evolve additional nucleic acid catalysts and such new catalysts are within the scope of the instant invention.

Example 2: Trans-cleaving Ribozymes

The self-cleaving ribozymes can be divided into separate ribozyme and substrate domains to create a functional bimolecular complex. This ribozyme presumably interacts with the substrate domain by forming base-paired regions that are analogous to helices I and II of the hammerhead ribozyme (FIG. 1). Likewise, the substrate specificity of ribozymes can presumably be altered by changing the sequences of the substrate-binding arms to complement the sequence of the desired substrate molecule, as was achieved with the ribozyme from clone 40 self-cleaving RNA (FIG. 5).

Figure 5:
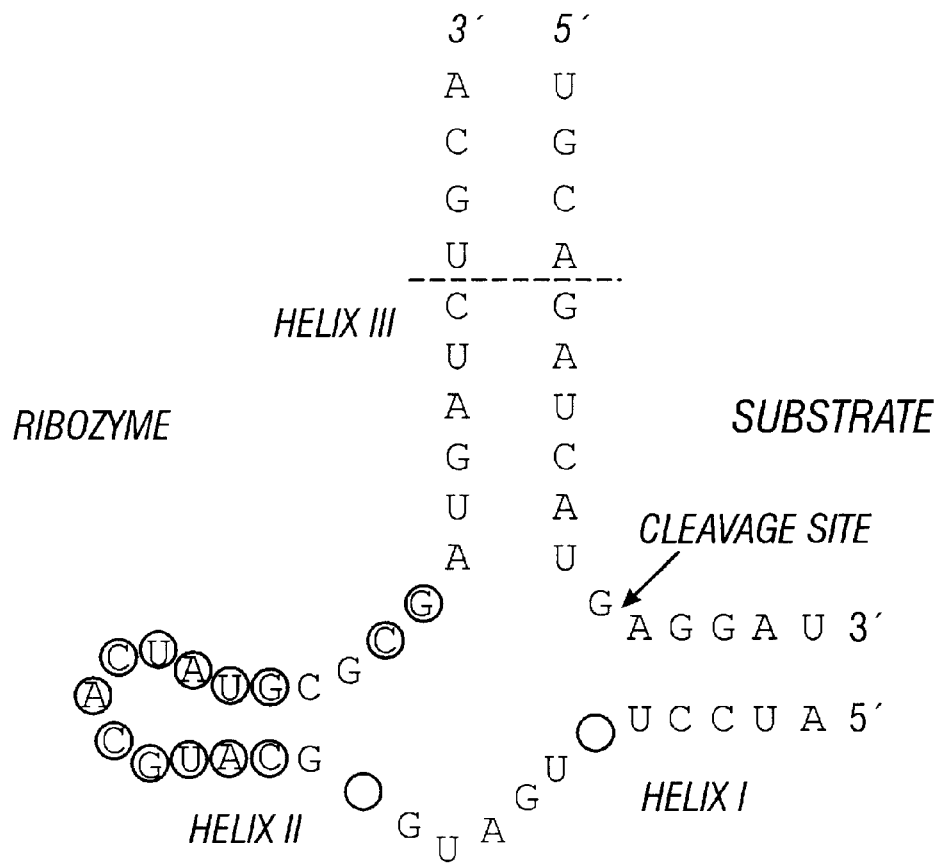
FIG. 5 shows sequence and possible secondary structure of a trans-cleaving ribozyme, SEQ ID NO: 26, and substrate SEQ ID NO: 25 of the invention. Arrow identifies the site of cleavage.
Figure 6:
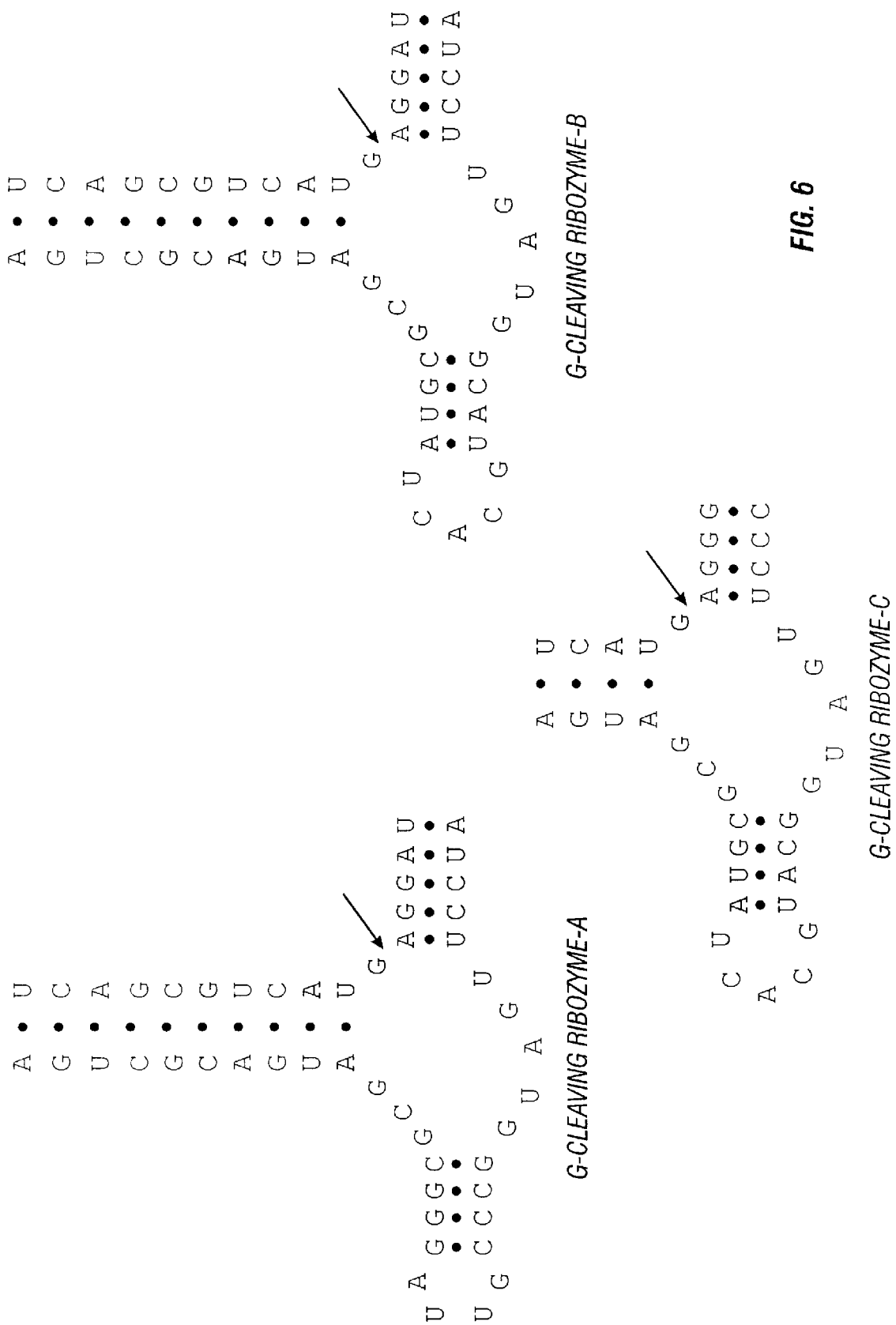
FIG. 6 shows non-limiting examples of trans-cleaving ribozyme-substrate complexes, SEQ ID NO: 27–32,of the present invention.
Figure 7:
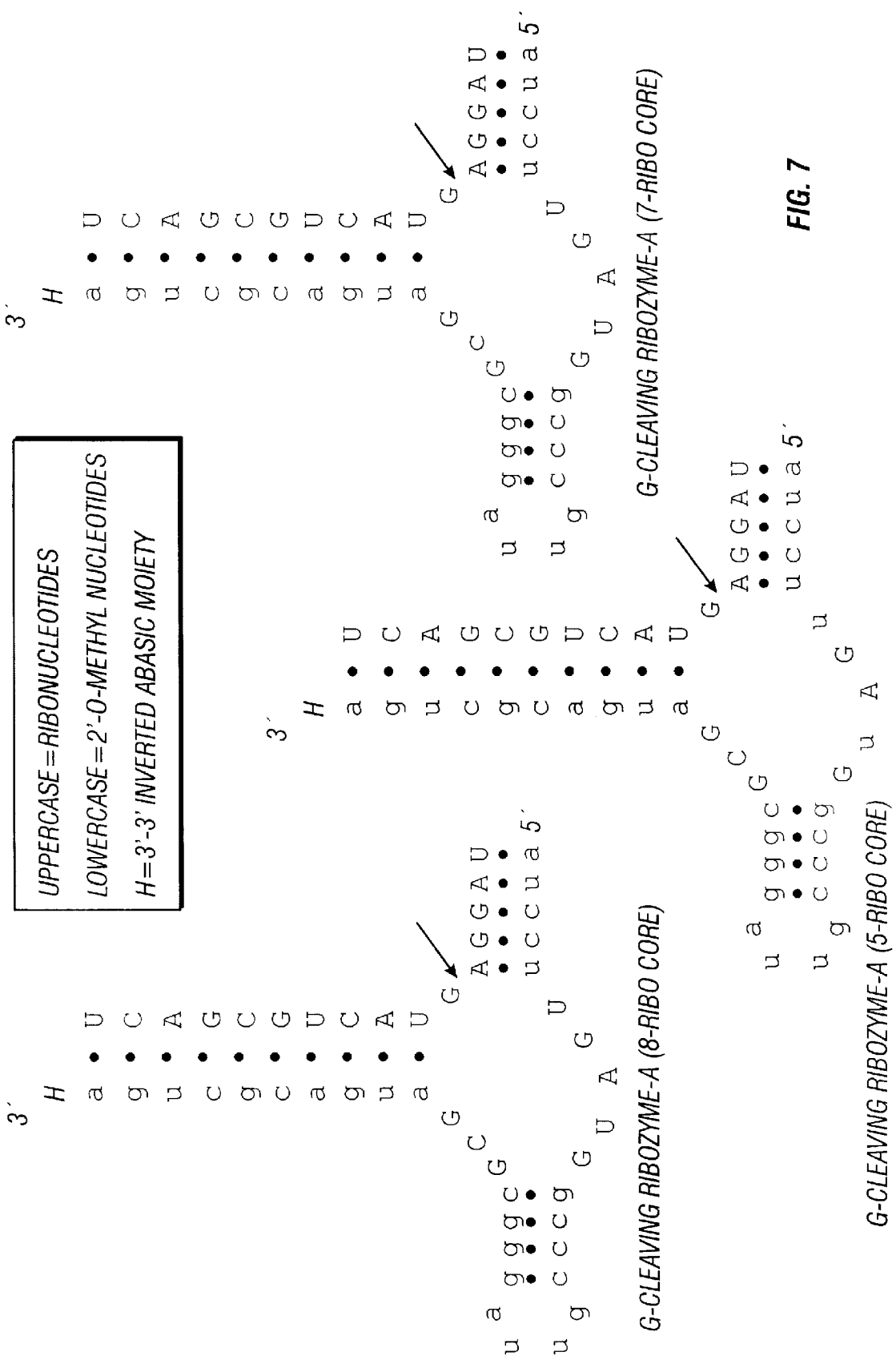
FIG. 7 shows non-limiting examples of chemically modified trans-cleaving ribozyme-substrate complexes, SEQ ID NO: 33–38 of the present invention.

To further characterize the selected ribozyme for intermolecular cleavage, Rz13/40 was divided into a catalytic portion and the corresponding substrate strand (FIG. 5). The initial ribozyme construct was designed with 5 bp each in stems I and III for annealing to the substrate. Stems of this length were chosen because they had been reported to give reliable kinetic data with the hammerhead. Cleavage kinetics of intermolecularly cleaving ribozymes was performed with chemically synthesized ribozyme and substrate in 50 mM Tris-HCl (pH 8.0), and 10 MM MgCl$_2$ with 50 to 500 nM ribozyme and 25 nM substrate for single turnover, and 50 to 500 nM substrate with 5 to 25 nM ribozyme for multiple turnover kinetics as described (Hertel et al., *Biochemistry* 33, 3374, 1994). The intermolecular version of Rz13/40 of the present invention gave a very high K$_M$, (1.1 mM) and low k$_{cat}$ (0.1 min$^{-1}$) under single turnover conditions and was inactive under multiple turnover conditions. As there was no doubt about the intramolecular cleavage of Rz13/40, the lack of catalytic activity under multiple turnover conditions must be associated with the design of the intermolecular version. After analysis of the ribozyme-substrate complex by native gel it was concluded that formation of the complex was inefficient under the conditions used.

A second ribozyme construct was synthesized, where stem III was extended to 10 base-pairs. Native gel analysis confirmed the formation of the ribozyme-substrate complex and the ribozyme cleaved its corresponding substrate efficiently under both single and multiple turnover conditions (Table II). The discrepancy between kcat and kcat' (0.06 and 0.91 min$^{-1}$ respectively) is presumably the result of product inhibition, which is a common effect observed with the native hammerhead. The time course of cleavage was followed for about 12 half-lives under single turnover conditions. Reactions were first order up to 60% cleavage within the first minute and reached a total of 80%. First order end points with the conventional hammerhead are commonly 70 to 75% (19). Steady state cleavage rates were linear for several turnovers. Although the hammerhead and class I ribozymes cleave at different internucleotide linkages (FIG. 1), both ribozymes appear to proceed by a similar chemical mechanism. The hammerhead ribozyme is known to produce a 2',3'-cyclic phosphate at the terminus of the 5'-cleavage product, thereby leaving a 5'-hydroxyl terminus on the 3'-cleavage fragment.

The site of substrate cleavage was confirmed as being behind G of the AUG cleavage triplet by comparison of the ribozyme cleavage product, obtained under single turnover conditions for 30 min, with the products of a limited alkaline hydrolysis of the 5'-end-labeled substrate and with a partial RNase T1 digest. Reactions were performed in 10 μl containing RNA, 50 mM Tris (pH 8) and CNPase (Sigma Chemicals) (0.62 u to 0.012 u/μl) and incubation at 45° C. for 1.5 h. Product analysis was on a 20% PAGE where the cyclic phosphate-terminated product runs slightly slower than the ring-opened derivative. In addition, the cleavage products were also shown to be the 2', 3'-cyclic phosphate and a 5'-hydroxyl by hydrolysis with CNPase and labeling with T4 PNK respectively. Thus Rz13/40 cleaves in a similar manner to the hammerhead. In order to investigate the properties and sequence requirements of the selected ribozyme Rz13/40, mutations were made on the substrate and ribozyme strands. In the native hammerhead, stem II has been shortened to as few as two base-pair without significant loss in activity. However, the removal of a single base-pair (10.3/11.3) in Rz13/40 resulted in a 1000-fold loss in activity for the cleavage behind an AUG triplet indicating the stem-loop structure has a wider role in catalysis.

The effect of mutations around the cleavage site have also been investigated under single and multiple turnover conditions (Table II). Surprisingly, the AUA triplet was also cleaved quite efficiently even though it was not selected for, again yielding a 2', 3'- cyclic phosphate. Triplets terminating in a uridine or cytidine were either cleaved extremely slowly or not at all. Thus this ribozyme is purine nucleoside specific. Whether this indicates a necessity for base pairing between $U^4$ and the nucleotide to be cleaved, as possible with AUG and AUA, is uncertain at present.

As the native hammerhead strictly requires a uridine in the middle of the triplet, it was of interest to test whether this was applicable to Rz 13/40. Interestingly the triplet AAG was cleaved with a $k_{cat}$ of 0.57 min$^{-1}$ under single turnover conditions, multiple turnover conditions showed a $k_{cat}$ of 0.09 min$^{-1}$. It was also tested whether the nucleotide next to the cleavage site was of importance. Cleavage of the triplet AUG with a following U or G was found to be only fractionally slower in single turnover than cleavage of AUG-A (Table II).

Inspection of the ribozyme sequences reveals some interesting features. The sequence 5'-GCGCG at positions 11.2 to 14 is present in all ribozymes from pool 10 onwards. This would indicate that this sequence may be an indispensable part for activity just as is the case for the GAA sequence in the conventional hammerhead.

Of the two classes of ribozyme isolated in Pool 13, the ribozymes with a deletion in the randomized region are the more active intramolecular cleavers. These ribozymes appear to have an overall secondary structure which is similar to that of the native hammerhead, but there are significant differences.

Obvious differences include the 'vacancies' at positions 3 and 9 in the core as well as the altered sequence to positions 12 to 14 already mentioned. More subtle differences are associated with stem-loop II. In the hammerhead a variety of structures are tolerated: the stem can be reduced to two base-pair, and the loop can be of virtually any size and even contain non-nucleotidic linkers. In the selected ribozymes similar to Rz13/40, less variation in the stem-loop structure is observed. In the active ribozymes of this class, stem-loop II consists of two G:C base-pairs adjacent to the core; followed by two A:U base-pairs; and finally terminating in a five nucleotide loop, where variations at only positions L2.4 and L2.5 have been detected. The length of the stem appears to have a large effect on catalytic efficiency, since the removal of a single base-pair (10.3/11.3) abolishes activity. The most active sequences in pool 13 have a fully complementary stem II. One mismatch at 10.2/11.2 as in Rz13/1 approximately halves the activity. It is interesting to note that in Pool 13, the more active ribozymes contain a deletion in the randomized region, which is 21 nucleotides instead of 22. Of these only Rz 13/31 and 13/29 show reasonable activity. One can draw a secondary structure for these with a stem II with two mismatches and the extra nucleotide in the core region.

The new triplet specificity should be usefull for the application of the ribozyme family of the present invention for the inhibition of gene expression in that it expands the targets on a mRNA for cleavage. Although the conventional NUX triplets might be considered sufficient for a wide application, the accessibility of oligodeoxynucleotides to mRNAs is very restricted. Thus the specificity of the new ribozyme for cleavage at purines, apparently independent of the nature of the neighboring nucleotides, should represent a considerable advantage over the native NUX-cleaving ribozyme for this application.

Diagnostic uses

Enzymatic nucleic acids of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention might have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the ribozyme is ideal for cleavage of RNAs of unknown sequence.

Other embodiments are within the following claims.

TABLE I 2.5 μmol RNA Synthesis Cycle

| Reagent | Equivalents | Amount | Wait Time* |
|---|---|---|---|
| Phosphoramidites | 65 | 163 μL | 25 |
| S-Ethyl Tetrazole | 23.8 | 238 μL | 25 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 80 | 1.18 mL | 45 sec |
| Acetonitrile | NA | 6.67 mL | NA |

*Wait time does not include contact time during delivery.

TABLE II

Rate constants for ribozyme 40 cleavage at various triplets with next nucleotide specified. Reaction conditions as in text. 1a, activity too low for quantitation; na, no activity detectable. MTO, multiple turnover; STO, single turnover

| | MTO kinetics | | STO kinetics |
|---|---|---|---|
| Cleavable Triplet | $k_{cat}$ (min$^{-1}$) | $K_M$ (nm) | $k_{cat}'$ (min$^{-1}$) |
| AUG-A | 0.06 | 50.71 | 0.91 |
| AUA-A | 0.09 | 24.70 | 0.34 |
| AUU-A | 1a | 1a | 0.007 |
| AUC-A | na | na | na |
| AAG-A | | | 0.57 |
| AUG-U | | | 0.35 |
| AUG-G | | | 0.66 |

What is claimed is:

1. A nucleic acid molecule with an endonuclease activity having the formula I:

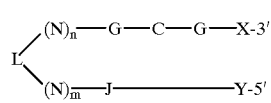

wherein, each N represents independently a nucleotide or an abasic moiety, which may be same or different; X and Y are independent oligonucleotides of length sufficient to stably interact with a target nucleic acid molecule; m and n are integers greater than or equal to 1, wherein if $(N)_m$ and $(N)_n$ are nucleotides, (N)m and (N)n may interact by hydrogen bond interaction; J is an oligonucleotide having a sequence selected from the group consisting of 5'-GGCAUCC-3', 5'-AGCAUU-3', 5'-GCAUCA-3', 5'-AGCAUC-3', and, 5'-AGCGUC-3'; L is a linker which may be present or absent, wherein said linker, when present, is a nucleotide linker or a non-nucleotide linker, or a combination of nucleotide and a non-nucleotide linker, wherein said nucleotide linker comprises a single-stranded region, or double-stranded region, or a combination of single-stranded and a double-stranded region; represents a chemical linkage; and C and G represent cytidine and guanosine nucleotides, respectively.

2. A nucleic acid molecule with an endonuclease activity having the formula II:

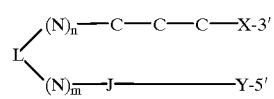

wherein, each N represents independently a nucleotide or a non-nucleotide linker, which may be same or different; X and Y are independent oligonucleotides of length sufficient to stably interact with a target nucleic acid molecule; m and n are integers greater than or equal to 1, wherein if $(N)_m$ and $(N)_n$ are nucleotides, (N)m and (N)n may interact by hydrogen bond interaction; J is an oligonucleotide of length 6 nucleotides having a sequence 5'-GGAAUC-3'; L is a linker which may be present or absent, wherein said linker, when present, is a nucleotide linker or a non-nucleotide linker, or a combination of nucleotide and a non-nucleotide linker, wherein said nucleotide linker comprises a single-stranded region, or double-stranded region, or a combination of single-stranded and a double-stranded region; represents a chemical linkage; and C represents cytidine nucleotide.

3. A nucleic acid molecule with endonuclease activity having the formula III:

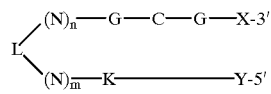

wherein, each N represents independently a nucleotide or a non-nucleotide linker, which may be same or different; X and Y are independent oligonucleotides of length sufficient to stably interact with a target nucleic acid molecule; m and n are integers greater than or equal to 1, wherein if $(N)_m$ and $(N)_n$ are nucleotides, (N)m and (N)n may interact by hydrogen bond interaction; K is an oligonucleotide of length 5 nucleotides having a sequence selected from the group consisting of 5'-UGAUG-3', 5'-UGAUC-3', and 5'-UGGGC-3'; L is a linker which may be present or absent, wherein said linker, when present, is a nucleotide linker or a non-nucleotide linker, or a combination of nucleotide and a non-nucleotide linker, wherein said nucleotide linker comprises a single-stranded region, or double-stranded region, or a combination of single-stranded and a double-stranded region; represents a chemical linkage; and C and G represent cytidine and guanosine nucleotides, respectively.

4. The nucleic acid molecules of any of claims 1–3, wherein said L in said nucleic acid molecule is nucleotide linker.

5. The nucleic acid molecule of claim 4, wherein said nucleotide linker is a nucleic acid aptamer.

6. The nucleic acid molecule of claim 5, wherein said aptamer is an ATP aptamer.

7. The nucleic acid molecule of any of claims 1–3, wherein said L is non-nucleotide linker.

8. The nucleic acid molecule of any of claims 1–3, wherein said (N)m and (N)n each have a nucleotide sequence.

9. The nucleic acid molecule of claim 8, wherein said nucleotide sequence of said (N)m is complementary to the nucleotide sequence of said (N)n.

10. The nucleic acid molecule of any of claims 1–3, wherein said nucleic acid cleaves a separate nucleic acid molecule.

11. The nucleic acid molecule of claim 10, wherein said separate nucleic acid molecule is RNA.

12. The nucleic acid molecule of claim 10, wherein said nucleic acid comprises between 12 and 100 bases complementary to said separate nucleic acid molecule.

13. The nucleic acid molecule of claim 10, wherein said nucleic acid comprises between 14 and 24 bases complementary to said separate nucleic acid molecule.

14. A cell including the nucleic acid molecule of any of claims 1–3, wherein said cell is not a living human.

15. The cell of claim 14, wherein said cell is a mammalian cell.

16. The cell of claim 15, wherein said cell is a human cell.

17. An expression vector comprising nucleic acid sequence encoding at least one of the nucleic acid molecule of any of claims 1–3, in a manner which allows expression of that nucleic acid molecule.

18. A cell including the expression vector of claim 17, wherein said cell is not a living human.

19. The cell of claim 18, wherein said cell is a mammalian cell.

20. The cell of claim 18, wherein said cell is a human cell.

21. A method of cleaving a separate nucleic acid comprising, contacting the nucleic acid molecule of any of claims 1–3 with said separate nucleic acid molecule under conditions suitable for the cleavage of said separate nucleic acid molecule.

22. The method of claim 21, wherein said cleavage is carried out in the presence of a divalent cation.

23. The method of claim 22, wherein said divalent cation is $Mg^{2+}$.

24. The nucleic acid molecule of claims 1–3, wherein said nucleic acid is chemically synthesized.

25. The expression vector of claim 17, wherein said vector comprises:

a) a transcription initiation region;

b) a transcription termination region;

c) a gene encoding at least one said nucleic acid molecule; and wherein said gene is operably linked to said initiation region and said termination region, in a manner which allows expression and/or delivery of said nucleic acid molecule.

26. The expression vector of claim 17, wherein said vector comprises:

a) a transcription initiation region;

b) a transcription termination region;

c) an open reading frame;

d) a gene encoding at least one said nucleic acid molecule, wherein said gene is operably linked to the 3'-end of said open reading frame; and wherein said gene is operably linked to said initiation region, said open reading frame and said termination region, in a manner which allows expression and/or delivery of said nucleic acid molecule.

27. The expression vector of claim 17, wherein said vector comprises:

a) a transcription initiation region;

b) a transcription termination region;

c) an intron;

d) a gene encoding at least one said nucleic acid molecule; and wherein said gene is operably linked to said initiation region, said intron and said termination region, in a manner which allows expression and/or delivery of said nucleic acid molecule.

28. The expression vector of claim 17, wherein said vector comprises:

a) a transcription initiation region;

b) a transcription termination region;

c) an intron;

d) an open reading frame;

e) a gene encoding at least one said nucleic acid molecule, wherein said gene is operably linked to the 3'-end of said open reading frame; and wherein said gene is operably linked to said initiation region, said intron, said open reading frame and said termination region, in a manner which allows expression and/or delivery of said nucleic acid molecule.

* * * * *